(12) United States Patent
Mapson et al.

(10) Patent No.: US 6,485,684 B1
(45) Date of Patent: Nov. 26, 2002

(54) FLUID CONNECTION SYSTEM FOR ENDOSCOPE REPROCESSING WITH CONTROLLED LEAKAGE

(75) Inventors: Tara Denise Mapson, Cleveland; Yury Keselman, Beachwood; David Jesurun, South Euclid; Victor M. Selig, Euclid; Joseph Tvergyak, Chardon; Richard A. Schieman, Novelty; Bruce L. Vavra, Wickliffe, all of OH (US); Joseph T. Sestak, Erie, PA (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/499,134

(22) Filed: Feb. 7, 2000

(51) Int. Cl.$^7$ .................................................. A61L 2/00
(52) U.S. Cl. ...................... 422/28; 206/210; 206/370; 206/438; 422/292; 422/297; 422/300
(58) Field of Search ................................ 422/300, 297, 422/292, 28; 206/210, 370, 438; 600/133

(56) References Cited

U.S. PATENT DOCUMENTS

| | | | |
|---|---|---|---|
| 4,281,674 A | 8/1981 | Tanaka et al. | |
| 4,299,244 A | 11/1981 | Hirai | 134/102 |
| 4,552,728 A | 11/1985 | Taylor | |
| 4,637,378 A | 1/1987 | Sasa | 128/4 |
| 5,279,799 A | 1/1994 | Moser | |
| 5,505,218 A | 4/1996 | Steinhauser et al. | 134/95.1 |
| 5,525,314 A | * 6/1996 | Hurson | 422/300 |
| 5,552,115 A | 9/1996 | Malchesky | 422/28 |
| 5,759,490 A | 6/1998 | Malchesky | |
| 5,833,935 A | 11/1998 | Malchesky | 422/300 |
| 5,843,388 A | * 12/1998 | Arroyo | 422/300 |
| 6,041,794 A | 3/2000 | Lin et al. | 134/22.11 |
| 6,068,815 A | 5/2000 | Oberleitner et al. | |

FOREIGN PATENT DOCUMENTS

| | | |
|---|---|---|
| DE | 3416743 | 7/1985 |
| DE | 3538744 | 4/1986 |
| EP | 0 835 665 | 4/1998 |
| EP | 0 945 140 | 9/1999 |

* cited by examiner

Primary Examiner—Krisanne Thornton
(74) Attorney, Agent, or Firm—Fay, Sharpe, Fagan, Minnich & McKee, LLP (57) ABSTRACT

A fluid disinfection or sterilization system includes spray nozzles (26) for spraying an anti-microbial fluid on the exterior of an endoscope (14) supported in a microbial decontamination chamber (10a, 10b). The endoscope includes interior lumens which are microbially decontaminated by flowing anti-microbial fluid from outlets (28) through the lumens. A port (36) is connected with a leak detector. In order to ensure that the proper leak detector and anti-microbial fluid ports of the disinfection or sterilization system are interconnected with the proper lumen ports of the endoscope, a tethered connection assembly (50) is provided. The tethered interconnection assembly includes fittings (60, 62, 64) which are uniquely configured for interconnection with an appropriate one of a high pressure port, a low pressure port, and the leak detector port. Fittings at the other end of the tube assemblies (56) are configured for interconnection with appropriate corresponding ports of the endoscope. The tube assemblies (56) are interconnected by a tether (52) to which plurality of plugs (58) for plugging appropriate ports of the endoscope are also connected. A tag (54) identifies the model(s) of endoscope that the tethered connection assembly is to be used with and provides a diagram showing the proper interconnection pattern.

32 Claims, 4 Drawing Sheets

FLUID CONNECTION SYSTEM FOR ENDOSCOPE REPROCESSING WITH CONTROLLED LEAKAGE

BACKGROUND OF THE INVENTION

The present application relates to the fluid handling arts. It finds particular application in conjunction with fluid sterilization and disinfection systems and will be described with reference thereto.

Fluid sterilization and disinfection systems are typically designed to cause microbes on the item to be removed or killed, i.e., microbially decontaminated, by a fluid anti-microbial agent. This is achieved in a variety of ways, including immersing the item in a bath of anti-microbial liquid, spraying the item with anti-microbial liquid, surrounding the item with anti-microbial vapor, and the like. While such systems work well for killing microbes on the exterior surface of the items to be decontaminated, internal lumens can be problematic. To be a viable commercial product, a sterilization or disinfection apparatus must provide assured contact between the anti-microbial agent and the microbes. On items with elongated lumens, such as endoscopes, it is desirable that the anti-microbial fluid assuredly contact all surfaces within the lumen. Typically, this is achieved by pumping or drawing the anti-microbial fluid through the lumen.

Often, endoscopes have a plurality of lumens which may have different cross-sections, length, internal obstructions, and the like. It is advantageous to supply the fluid to different lumens at different pressures. Further, some lumens have multiple openings. Typically, plugs are inserted into or over some of the openings to force the anti-microbial fluid to flow the entire length of the lumen. Often, endoscopes have a lumen which does not need to be sterilized and worse yet, can be damaged by contact with fluids. Further, the lumens have a variety of connector styles, such as screw threads, bayonet pipe connectors, and the like, as well as different diameters.

Typically, the sterilization technicians are given a variety of individual plugs and fittings from which they select the most appropriate plugs and fittings for a specific endoscope to be sterilized or disinfected. Being small parts, they are sometimes lost. The technicians, in many cases, improvise by using another part which appears to work. In other cases, the technicians merely make a mistake in selecting fittings or plugs or in making the connections between the fluid supply, fittings, and lumens. When improper plugs or fittings are used and when improper interconnections are made, the assurance that the anti-microbial agent is contacting all microbes within the lumens is lost.

The fittings and plugs typically connect securely with the structures at the lumen ports. At the surfaces of interconnection, microbes can become trapped between the fittings or plugs and the structures at the lumen port. When there is a good frictional fit, the frictional fit protects these microbes from the anti-microbial agent. This creates the possibility that at the end of the cycle there may be active microbes on the surfaces adjacent the lumen ports destroying the assurance of disinfection or sterility. One solution to the trapped microbe problem is shown in U.S. Pat. Nos. 5,552,115 and 5,833,935 of Malchesky in which the fittings and plugs are made of an open-celled plastic material. The porous fitting solution is effective, but does have some drawbacks. First, the porous plastic material is relatively soft. With repeated use, dimensions can change altering flow characteristics. Moreover, the plastic can be damaged or broken during use, again altering flow characteristics. After a disinfection or sterilization cycle, the fittings are typically wet with water from the final rinse. Wet, porous materials can become breeding grounds for airborne microbes if not handled properly. One use, disposable porous connectors and fittings can be costly and there is no assurance that the operator will use a new fitting in each cycle rather than reusing an old one.

The present invention provides a new and improved method and apparatus which overcomes the above-referenced problems and others.

SUMMARY OF THE INVENTION

In accordance with one aspect of the present invention, a fluid disinfection or sterilization system is provided. A chamber receives a lumened article to be microbially decontaminated. A plurality of fluid outlets in the chamber direct an anti-microbial fluid over exterior surfaces of the article. A plurality of fluid ports in the chamber discharge the anti-microbial fluid to supply it to interior lumens of the article. A tethered connection assembly provides for interconnection of the lumens of the article and the fluid ports. The tethered assembly includes a first tube assembly having fittings at its ends. One of the fittings is configured for interconnection with one of the fluid ports and the other fitting is configured for interconnection with a lumen of the article. The tethered connection assembly further includes at least one of (i) a second tube assembly with fittings and (ii) a plug configured for interconnection with a lumen of the article. A tether interconnects the tube assemblies and plugs.

In accordance with another aspect of the present invention, a tethered interconnection assembly is provided for interconnecting lumens of endoscopes with anti-microbial fluid discharge ports of a fluid disinfection or sterilization system. At least one tube assembly includes a tube, a fitting at one end configured for interconnection with an anti-microbial fluid discharge port, and a fitting at another end configured for interconnection with surfaces surrounding a lumen port on the endoscope. At least one plug is configured for interconnection with the surfaces surrounding one of the endoscope lumen ports. A tether is connected with the tube assemblies and the plug. At least one indicia is associated with the tether for indicating at least one of a model of endoscope and a family of endoscope models with which the tether assembly is to be used.

In accordance with another aspect of the present invention, a fluid disinfection or sterilization system is provided. A chamber receives a lumened article to be microbially decontaminated. A plurality of first fluid outlets in the chamber directs anti-microbial fluid over exterior surfaces of the article. At least one second fluid outlet discharges anti-microbial fluid and is configured for interconnection with a first fitting. A tube assembly interconnects the second fluid outlet with surfaces adjacent a port to a lumen in the article. The tube assembly includes a tube to which the first fitting is connected. A second fitting is connected with the tube and configured for loose interconnection with the surfaces adjacent the lumen port. The interconnection is in such a manner that (i) most of the anti-microbial fluid flows into the lumen and (ii) a fraction of the anti-microbial fluid flows between the fitting and the surfaces adjacent the lumen port. The interconnection is sufficiently loose that the fitting wobbles, changing momentary points of contact with the surfaces adjacent the lumen port.

One advantage of the present invention resides in the anti-microbial fluid's assured contact with the surfaces abutting the fittings and plugs.

Another advantage of the present invention is that it promotes the use of the proper fittings and plugs with each endoscope.

Another advantage of the present invention is that it is easy and convenient to use.

Another advantage of the present invention resides in consistent, repetitive operation.

Another advantage of the present invention is that it provides anti-microbial fluid flow through deadend passages.

Another advantage of the present invention is that it assures that the fittings and plugs are correctly matched to each type of endoscope.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not be construed as limiting the invention.

DETAILED DESCRIPTION OF THE PREFERRED EMBODIMENTS

Figure 1:
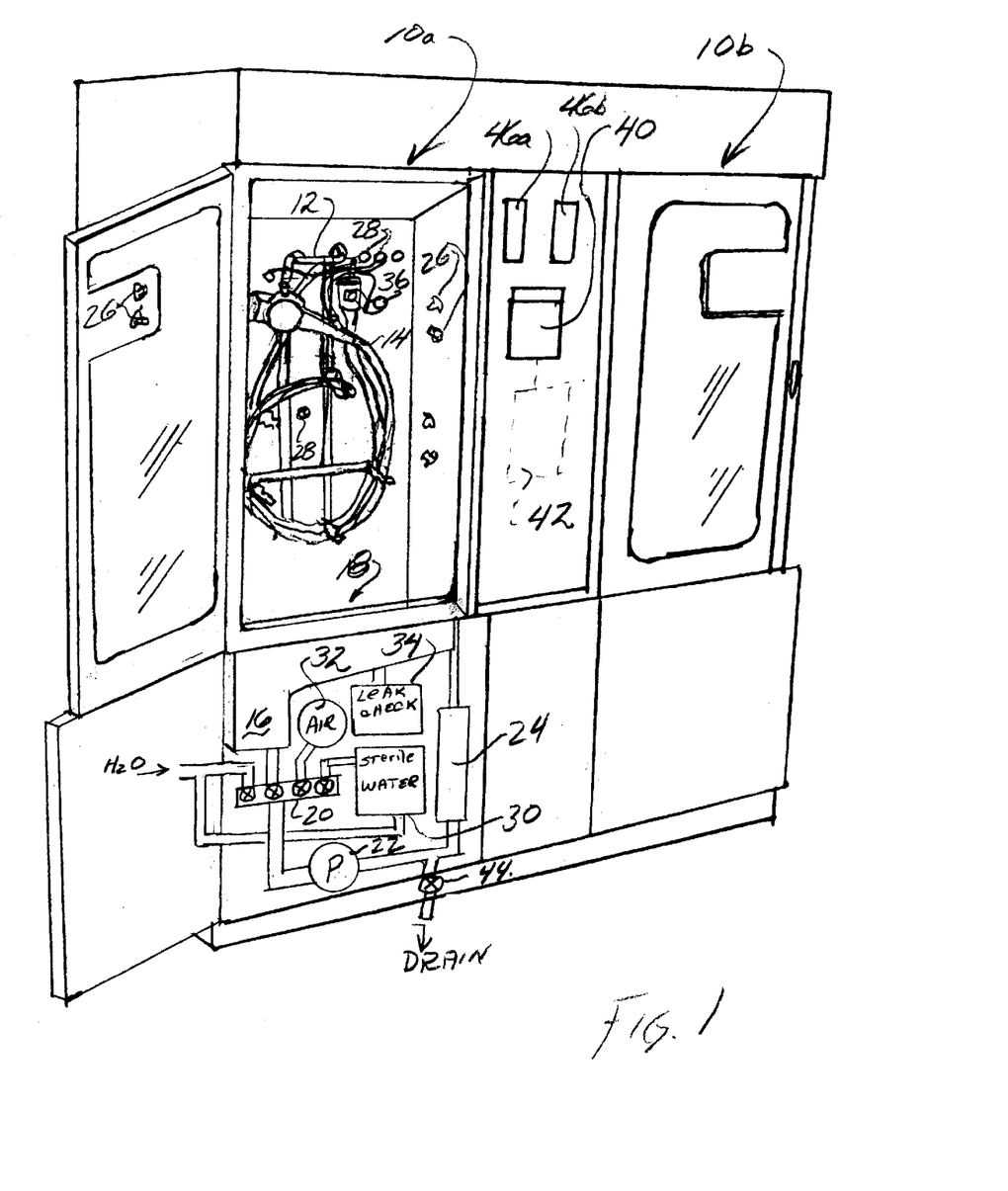
FIG. 1 is diagrammatic illustration of an exemplary fluid disinfection/sterilization system in accordance with the present invention.

With reference to FIG. 1, a liquid washing and microbial decontamination system includes a pair of chambers 10a, 10b for washing and microbially decontaminating endoscopes and other goods. Chamber 10a is described in detail, but it is to be appreciated that chamber 10b is analogous. A rack 12 having a plurality of pegs around which the tubes of the endoscope 14 are wound is supported in the chamber. The rack can be hung in the chamber and the endoscope wrapped around it or the endoscope can be wrapped around the rack at a remote location and then the rack and scope are hung as a unit in the chamber. A cup or other ampule containing a washing solution, such as detergent, corrosion inhibitors, and an anti-microbial agent is loaded in a well 16 defined in a lowermost point of a sump 18 at the bottom of the chamber.

A manifold 20 permits any of a plurality of fluids to be connected with a pump 22. In one state, the manifold connects outside water to the pump 22 which pumps the water through a heater 24 to nozzles 26 located around the chamber and fluid outlet ports 28 located in a rear wall of the chamber. Preferably, some of the ports 28 are high pressure ports and others are low pressure ports. Each of the ports includes a valve that has an open state and a leaky closed state that permits limited fluid flow to assure circulation through the tubing branch leading to it. In another state, the manifold 20 connects the pump with the well 16 at the bottom of the sump to recirculate fluid. In another state, the manifold connects the pump with a sterile water generator 30. In yet another state, the manifold connects the nozzles (either through the pump or directly) with a source of sterile air 32, preferably under pressure.

A leak detector 34 is connected with a leak test port 36. The leak detector checks whether a lumen or other structure connected with port 36 is leaking, e.g., whether it holds a preselected vacuum or positive pressure.

It is to be appreciated that analogous elements are connected with the second chamber 10b, although a common sterile water generator can supply both systems. A common operator input device 40, such as touch screen, enables the operator to put processing instructions into a common control 42 for the two chambers. The common control causes the leak check device to check whether the lumen connected with the port 36 is leaking or not. The automatic control also controls the manifold 20 and a cup opening device (not shown) in the well 16, the pump 22, the heater 24, and a drain valve 44. A typical cycle includes pumping cold water to the spray nozzles and the interior lumen ports to remove gross debris, after which the water is drained. Next, a washing solution section of the cup in the well 16 is opened as new water is brought in and circulated to the nozzles and the ports to wash the interior and exterior of the endoscope. After the wash and drain cycle, another rinse cycle removes excess detergent or other washing compounds. After the rinse is drained, air is blown through at least the outlet ports 28 and the interior lumens of the endoscope to remove excess fluid. A corrosion inhibitor compartment of the cup is then opened as additional water is brought into the system. The corrosion inhibitors, buffers, and other components in solution are circulated to the nozzles and output ports. Thereafter, a microbicide portion of the cup is opened to release a microbicide into the circulating solution. After the anti-microbial solution is drained, air again blows excess liquid from the lumens of the endoscope. One or more sterile water rinses follow concluding with a blow out of the water from the lumens. At the end of the cycle, the controller 42 causes an appropriate one of printers 46a, 46b to print out a record of the completed sterilization or high level disinfection cycle.

Figures 2, 3:
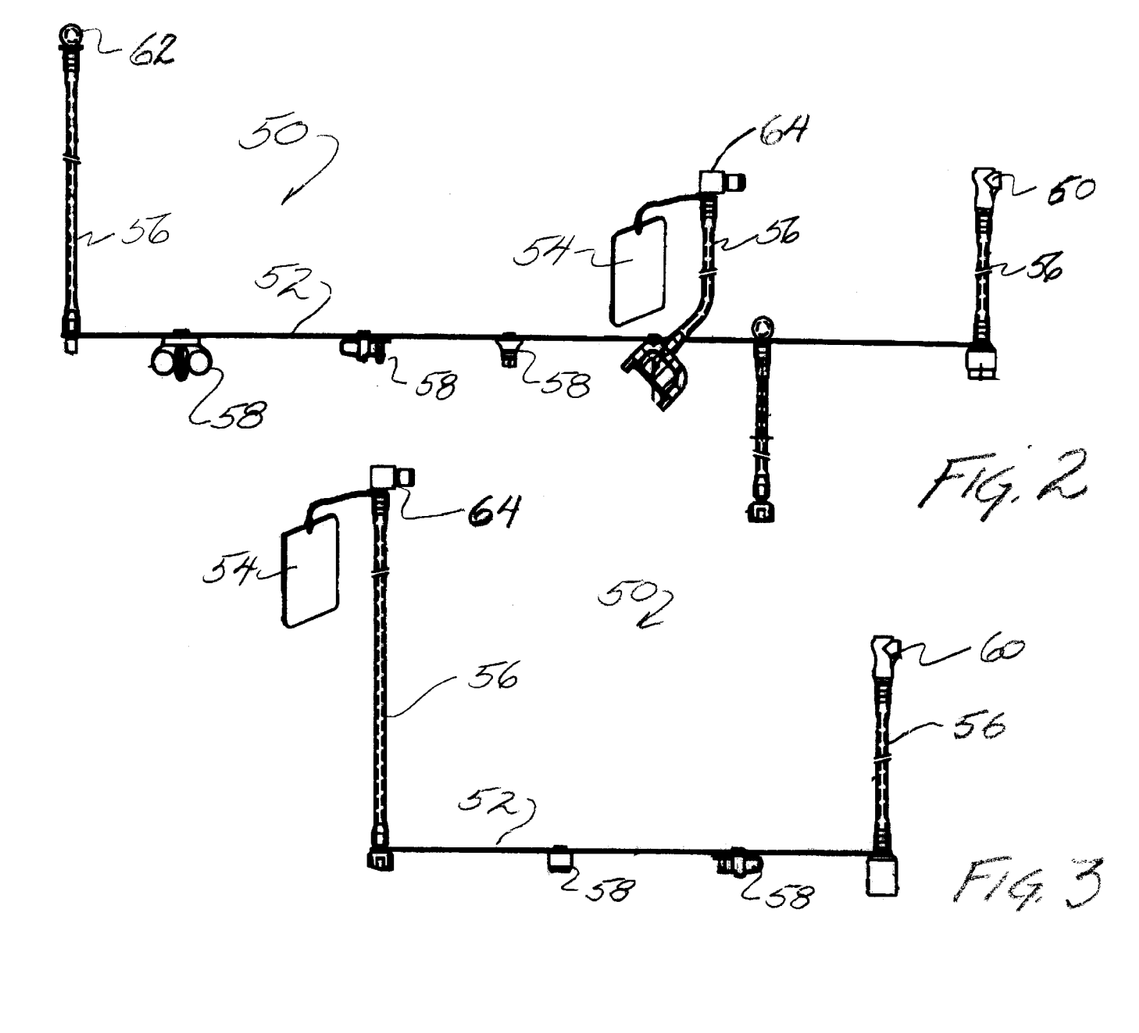
FIG. 2 is a detailed view of an exemplary tethered fitting and plug assembly in accordance with the present invention.
FIG. 3 illustrates another tethered plug and fitting assembly.
Figure 2:
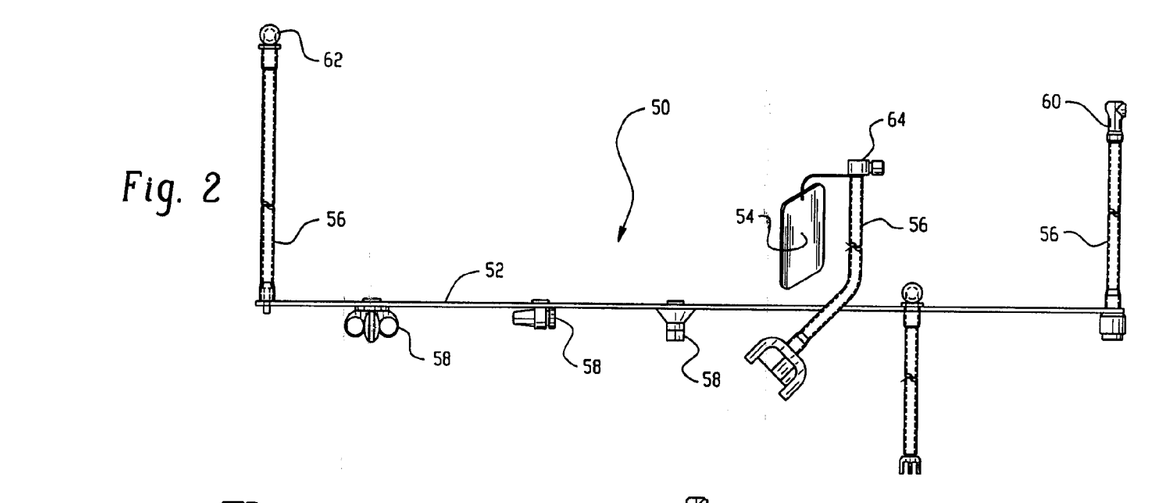
Figure 3:
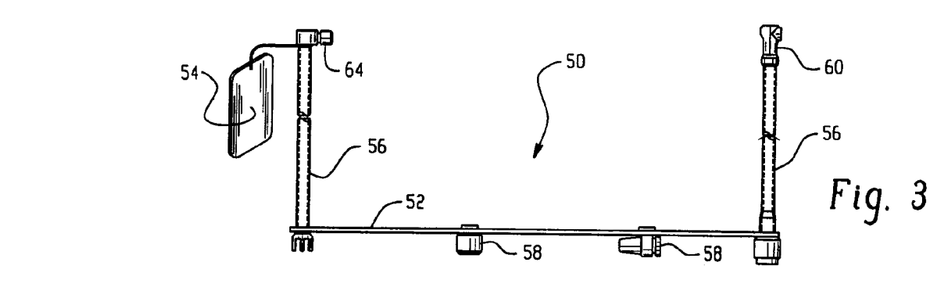

With continuing reference to FIG. 1, and further reference to FIGS. 2 and 3, after the endoscope 14 is mounted on the rack 12 in the chamber, the operator uses a tethered set of connectors and plugs 50 to interconnect various ports of the endoscope with the liquid ports 28 and the leak detector port 36 and to plug various ports of the endoscope. More specifically, each of the tethered plug and connector assemblies 50 includes a tether 52 which is connected to a tag 54. The tag 54 carries an indicia of the model or family of models of endoscope which are to be used with tethered set of plugs and connectors. The tag further includes a diagram illustrating how each of the connectors is to be interconnected between the scope and the outlet ports 26 and the leak detector ports. Step by step instructions are also included. Each of the connectors 56 or plugs 58 include a sequential reference character, such as a number or letter, which identify each connector and each plug and correlate the connectors and plugs with the instructions and the order in which they are to be connected.

Typically, one of the connectors 56 has a fitting 60 which is configured to mate only with the leak test port 36. The other end of the connector has an appropriate fitting for interconnection with the leak test port of the endoscope. The fluid ports 28 preferably include high pressure ports and low pressure ports. Optionally, the ports may have a larger number of dedicated pressures. Another of the connectors typically has a fitting 62 which is configured to be connected only with one of the high pressure fluid ports 28; while other connectors have a fitting 64 configured to be connectable only with one of the low pressure output ports 28. Various techniques may be utilized to limit each fitting to be connected with only specific one or ones of the ports 28, 36, such as different diameters, different connecting mechanisms (threaded, bayonet, etc.), different shapes, and the like. The plugs 58 are each configured to mate with the appropriate ports on the scope identified by the tag. The length of the tether and the length of portions of the tether between the various plugs and connectors are selected such that each of the connectors and fittings just reach a port of the endoscope to which they are to be connected. In this manner, if one of the connectors or plugs is connected with the wrong port, the tether will be too short for other connectors or plugs to reach an available port on the endoscope. This provides a ready indication to the operator that the plugs and fittings have not been connected properly or that the wrong tether assembly has been selected.

A wide variety of plugs and fittings are connected with the various tethers. Different endoscope manufacturers, and even the same manufacturer within different families of endoscopes, use different types and sizes of port structures. The appropriate fittings and plugs for each of the outlet port structures is preassembled on the tether. Although each of the fittings and plugs is configured to conform with the outlet port structure on the intended endoscope, they are not designed to couple in a fluid-tight connection. To the contrary, the fittings (other than leak test fittings) and plugs are designed to allow limited leakage between their structure and the port structure of the endoscope to which they are mounted. While the fittings and plugs may touch the port structure in some positions at some points, vibration, water flow, and pressure variations cause sufficient movement that the point of contact shifts and all points on the port structure of the endoscope are subject to the anti-microbial fluid during a significant portion of the cycle. Preferably, the nozzles 26 operate in sets. That is, one group of nozzles operates for awhile, and then shuts off as another group of nozzles starts operating. This change in spray direction again assists in rocking the fittings and plugs in the associated endoscope port structure.

Figure 4:
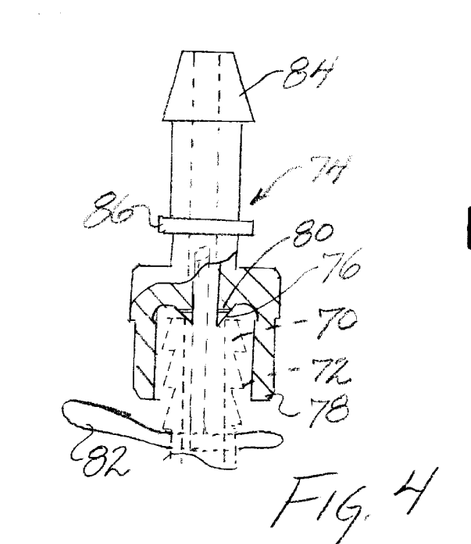
FIG. 4 illustrates the interconnection between one of the tethered fittings and a port (shown in phantom) on an endoscope.

With reference to FIG. 4, many endoscope ports are defined by extending tubular elements 70 with exterior barbs 72. A fitting 74 includes a body portion that defines a beveled annular ring 76 designed to be engaged partially into the interior of the tubular element 70. A plurality, e.g., four peripheral leg members 78 surround and are spaced from the exterior of the barbs to maintain alignment and prevent excessive tipping. A plurality of small passages 80 cause a small amount of fluid to be ejected under relatively high pressure and flow over the barbs 72. Additional fluid flows between the beveled surface 76 and the tubular element 70. A wire bail 82 is dimensioned to pass under the last of the barbs 72. The distance between the wire bail and beveled surface 76 is selected to be just slightly longer than the corresponding distance on the fitting such that an annular gap forms between the beveled surface 76 and the port and between the bail and the barbs, although both will make contact from time to time. The housing body further includes a barbed element 84 for interconnection with tubing of the appropriate length for interconnection with the fluid ports. Again, the tubing just reaches the appropriate fluid port 28 to provide an indication that it has been properly connected to the scope. A collar element 86 provides a stop for the tubing and provides a detent over which the tether 52 is fit.

Figure 5:
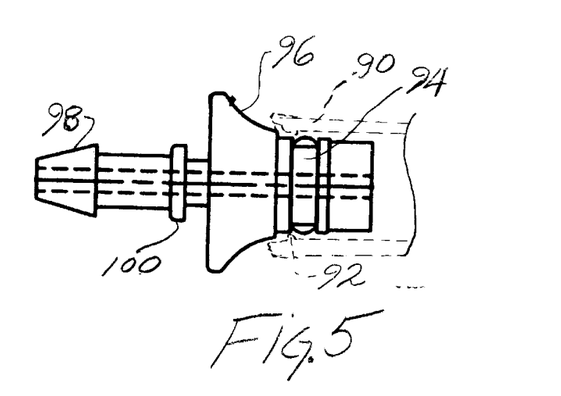
FIG. 5 illustrates another fitting for interconnection between a tubing assembly and an endoscope port.

With a reference to FIG. 5, some endoscope port structures include a tubular segment or internal bore 90 which has a small inward projecting lip or detent 92. A housing body includes an annular groove in which a C-ring 94 is loosely retained. The C-ring is sufficiently spaced from the body that it can be compressed as it snaps past the lip 92. Preferably, the C-ring spans about 300° of arc. The C-ring and a shoulder portion 96 of the body are spaced further than the thickness of the lip such that there is in and out play between the tube or bore 90 and the fitting. The fitting further includes a barbed tubular element 98 for interconnection with a length of tubing. A shoulder 100 provides a stop for the tubing and a detent over which the tether 52 is received.

Figure 6:
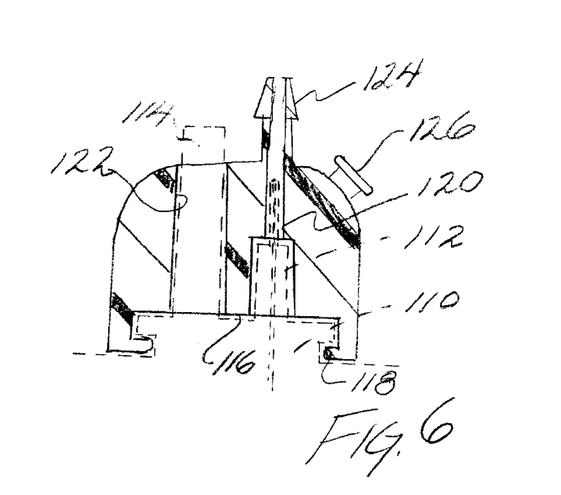
FIG. 6 is a cross-sectional view of another fitting for interconnection with an endoscope port.

With reference to FIG. 6, some endoscopes have raised port structures 110 supporting both a tubular structure 112 and a post 114. The fitting includes a fitting body having a lower surface 116 and inwardly projecting detents or arc segments 118 for snapping or twisting under a lip on the structure 110. The spacing between the bottom surface 116 and the detents 118 is again slightly larger than the thickness of the lip of the raised portion 110 to provide a thin fluid flow path therebetween. The body further defines a bore 120 which is dimensioned just larger than the tubular pipe 112 such that most of the fluid flow flows down its bore. A small amount flows around the periphery. A second bore 122 is again slightly larger in diameter than the post 114 to form a narrow angular cap therebetween. A portion of the fluid flowing between the bottom surface of housing and the mounting element 110 flows through the bore. Again, the dimensions are sufficiently loose that the fitting is movable short distances longitudinally and along canting directions. The fitting again includes a barb 124 for interconnection with associated tubing and a post 126 for interconnection with the tether 52.

Figure 7:
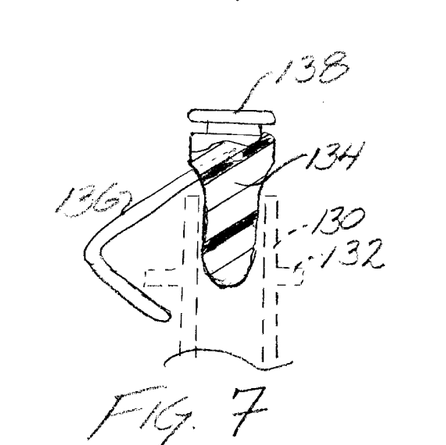
FIG. 7 is an elevational view in partial section of a plug assembly for interconnection with an endoscope port.

With reference to FIG. 7, some ports are defined by tubular elements 130 having an annular collar 132. When it is appropriate to plug these ports, one type of plug includes a housing body that tapers into an extension 134 slightly smaller in diameter than the interior bore of the tubular element 130. A wire bail 136 is pivotally connected to the body to snap under the collar 132. Again, the dimensions are such that during normal vibration, fluid flows between the plug and the tube and fluid flows between wire bail 136 and the collar 132. An enlarged portion 138 is again provided for receiving the tether 52.

Figure 8:
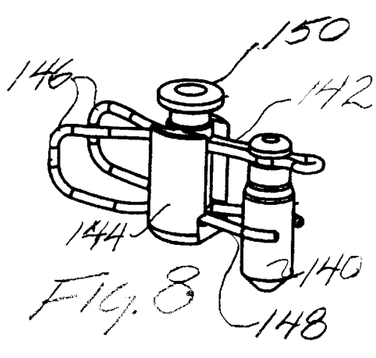
FIG. 8 is a perspective view of yet another plug assembly for interconnection with an endoscope port.

Reference to FIG. 8, for easier connection and disassembly, a plug includes a plug element 140 which is slightly smaller in diameter than the bore of the port to be plugged. The plug is connected by wire member 142 with a body portion 144. A pair of wire handles 146 are pivotally connected through the body portion with a pair of wires to form gripping elements which engage a groove in or under the underside of a lip surrounding the port. In this manner, by squeezing and releasing the handles 146, the plug can be inserted into the port and wire spring elements 148 can hold it loosely in place. A button 150 provides a convenient interconnection with the tether 52.

Figure 9:
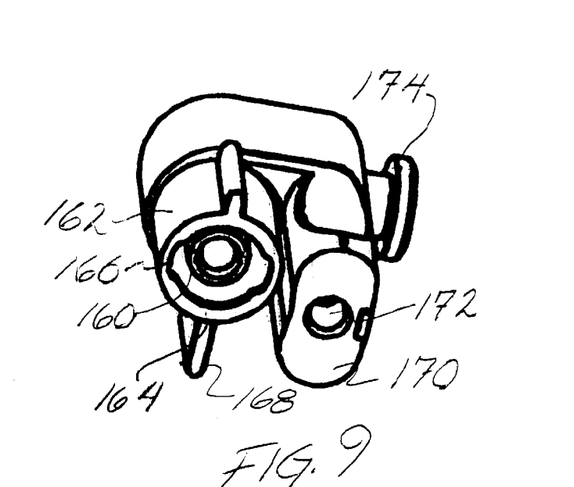
FIG. 9 is a perspective view of a plug assembly for interconnection with a pair of endoscope ports.

With reference to FIG. 9, some ports are surrounded by a tubular element having a pair of outward detents for a bayonet type interconnection. A plug housing body includes a tapered annular surface 160 analogous to surface 76 of FIG. 4. The body further includes a rotatable portion 162 having an inward directed flange 164 with a pair of cutouts 166 for receiving the projecting detents on the port. After the detents are received through the cutout portion 166, the operator engages a handle portion 168 and rotates rotatable portion 162 by a quarter turn to lock it in place over the fitting. Again, the dimensions are such that the plug wobbles sufficiently to provide flow over all surfaces. In some endoscopes, a projecting tubular element is disposed adjacent the other port. To this end, the housing body further includes a section 170 having a bore 172 of just slightly larger diameter than the tube to be received. Where appropriate, an internal bore extends between the bore 172 and the interior of the conical surface 160 to provide a controlled fluid flow path between the two ports. A button 174 provides a convenient connection point for the tether.

Figure 10:
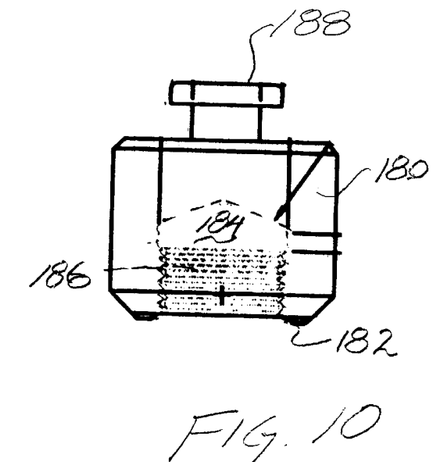
FIG. 10 is an elevational view of another plug assembly for interconnection with an endoscope port; and, FIG. 11 is a perspective view of yet another plug assembly for interconnection with a pair of adjacent ports of an endoscope.

With reference to FIG. 10, a plug includes a housing body 180 having two projecting feet 182 to hold the plug away from an associated surface of the endoscope. The plug body has an interior bore 184 that is internally threaded with non-sealing threads 186. NPT threads are designed for a fluid tight seal, but other standard threads, e.g., acme threads, are not. The threads may also be redimensioned such that they leave gaps as they loosely engage the threads of the scope port. Wobble between the threads provides changing fluid flow paths through the threaded connection. Optionally, sections of the threads may be removed to create an enlargement 186 in one more locations down the side of the internal bore to provide for less restrictive fluid flow. The contact points 182 prevent the threads from being screwed down so tight that fluid is not permitted to flow between the bottom of the housing and the endoscope, and preventing closing of the gaps between the threads of the fitting and the threads of the endoscope. A button 188 provides a convenient mounting point for the tether 52.

Figure 11:
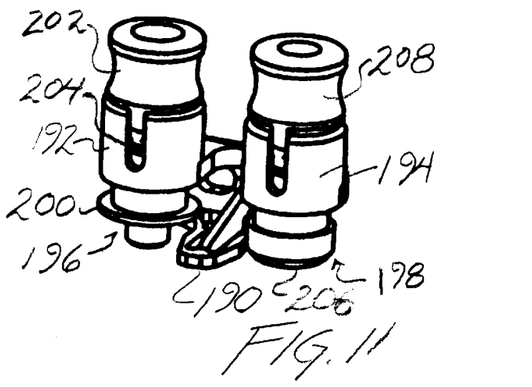

With reference to FIG. 11, on some endoscopes there are pairs of ports to be plugged. In the embodiment of FIG. 11, the housing body includes a lower tab 190 which slides under outward extending lips on a pair of tubes on an associated structure. The body defines a pair of cylinders 192, 194 in which plungers 196, 198 are mounted. The plunger 196 is smaller in diameter than the tube to be plugged with a surrounding flange 200 of a diameter a little smaller than the internal diameter of the bore in which it is received. A spring (not shown) within the housing 192 biases the plug into the opening. A handle portion 202 enables the plug to be pulled up against the biasing portion of the spring. When pulled up and rotated, a detent 204 moves out of the corresponding slot to hold the plunger retracted. The plunger 198 has a beveled lower edge 206 which is biased against the surrounding edge of the scope port by a spring (not shown) in the housing 194. A handle 208 again enables the plunger 198 to be retracted and, when turned, held retracted. In this manner, the operator retracts both plungers and slides the tab 190 underneath surrounding lips. The two plungers are then released under the spring bias. The plunger handles 202 and 208 are dimensioned such that, upon release, they stop on the housing cylinders 192 and 194 before the plungers 196 and 198 contact the device, leaving a gap which allows fluid to flow around the port.

The above discussed fittings and tabs are exemplary only. Numerous additional leaky connections are contemplated. New and improved endoscopes are introduced regularly. The new and improved endoscopes in many instances will have different port configurations which require modifications to the foregoing exemplary fittings and plugs.

The clearance between the plug and the surrounding structure on the endoscope also varies with the degree of stoppage or leakage that is appropriate to the application. In some situations, it is desirable to allow the plug to pass a sufficient amount of fluid that the pressure downstream in the lumen is reduced to a preselected fraction of the upstream pressure. When such a pressure reduction is desired, the clearances between the plug and the endoscope are increased. Optionally, the plug may have a controlled leakage or feedback port or passage.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A fluid disinfection or sterilization system comprising:
   a chamber for receiving a lumened article to be microbially decontaminated;
   a plurality of fluid outlets in the chamber for directing an anti-microbial fluid over exterior surfaces of the article;
   a plurality of fluid ports in the chamber through which the anti-microbial fluid is suppliable to interior lumens of the article;
   a tethered connection assembly for selective interconnection with the lumens of the article and selective interconnection with the fluid ports, the tethered assembly including:
      a first tube assembly having fittings at its ends, one fitting configured for selective interconnection with one of the fluid ports and the other fitting configured for selective interconnection with a lumen of the article;
      a second tube assembly with fittings configured for selective interconnection with a second of the fluid ports and a second lumen of the article; and,
      a flexible tether which interconnects the first and second tube assemblies.

2. A fluid disinfection or sterilization system comprising:
   a chamber for receiving a lumened article to be microbially decontaminated;
   a plurality of fluid outlets in the chamber for directing an anti-microbial fluid over exterior surfaces of the article;
   a plurality of fluid ports in the chamber through which the anti-microbial fluid is suppliable to interior lumens of the article;
   a leak detector port in the chamber interconnected with a leak detector;
   a tethered connection assembly for interconnection with the lumens of the article and the fluid ports, the tethered connection assembly including:

a first tube assembly having fittings at its ends, one fitting configured for selective interconnection with one of the fluid ports and the other fitting configured for interconnection with a lumen of the article, an additional tube assembly having a fitting at one end configured for selective interconnection with the leak detector port but not with the fluid ports and another fitting at an opposite end configured for interconnection with a lumen of the article, and a tether which interconnects the first tube assembly and the additional tube assembly.

3. The fluid disinfection or sterilization system as set forth in claim 1 wherein the article to be microbially decontaminated is an endoscope.

4. A fluid desinfection or sterilization system comprising:

a chamber for receiving endoscopes to be microbially decontaminated;

a plurality of fluid outlets in the chamber for directing an anti-microbial fluid over exterior surfaces of the endoscope;

a plurality of fluid ports in the chamber through which the anti-microbial fluid is suppliable to interior lumens of the endoscope;

a plurality of tethered connection assemblies, each one of the tethered connection assemblies being for interconnection between the lumens of a preselected model of endoscope or one of a family of endoscope models which is to be microbially decontaminated and the fluid ports, the tethered connection assemblies each including:

a first tube assembly having fittings at its ends, one fitting configured for selective interconnection with one of the fluid ports and the other fitting configured for selective interconnection with a lumen of the article, at least one of (i) a second tube assembly with fittings and (ii) a plug configured for selective interconnection with a lumen of the article, a tether which interconnects the tube assemblies and plugs, and a tag which identifies at least one of (i) the model of endoscope or (ii) the family of endoscope models with which the tethered connection assembly is to be utilized.

5. The fluid disinfection or sterilization system as set forth in claim 4 wherein the tag further includes:

a diagram illustrating proper interconnection of the tethered tube assemblies and plugs with the fluid ports and the lumens of the endoscope.

6. The fluid disinfection or sterilization system as set forth in claim 4 wherein the tethered connection assembly includes a plurality of tube assemblies and a plurality of plugs, all interconnected with the tether.

7. The fluid disinfection system as set forth in claim 6 wherein each of the tube assemblies and plugs includes an indicia of interconnection order and is attached to the tether in accordance with the interconnection order.

8. A fluid disinfection or sterilization system comprising:

a chamber for receiving an endoscope to be microbially decontaminated;

a plurality of fluid outlets in the chamber for directing an anti-microbial fluid over exterior surfaces of the endoscope;

a plurality of fluid ports in the chamber through which the anti-microbial fluid is suppliable to interior lumens of the endoscope;

a tethered connection assembly for interconnection with the lumens of the endoscope and the fluid ports, the tethered assembly including:

a plurality of tube assemblies, each assembly having fittings at its ends configured for interconnection with the fluid ports and a lumen of the endoscope, at least one plug configured for interconnection with a lumen of the endoscope, a tether which interconnects the tube assemblies and at least one plug, the tether including a strap, the tube assemblies and plugs being interconnected with the tether strap in an appropriate order and spacing such that the tether strap allows each of the plugs and tube assemblies to just reach a corresponding lumen on the endoscope while not reaching sufficiently far for at least some of the tube assemblies and plugs to reach non-corresponding lumens on the endoscope.

9. The disinfection or sterilization system as set forth in claim 8 wherein the tube assembly fittings and the plugs are configured to be sufficiently loosely received in structures defining ports to the lumens as to provide a thin gap therebetween such that anti-microbial fluid flows between the fittings and plugs and the structures defining the lumen ports.

10. A disinfection or sterilization system comprising:

a chamber for receiving a lumened article to be microbially decontaminated;

a plurality of fluid outlets in the chamber for directing an anti-microbial fluid over exterior surfaces of the article;

a plurality of fluid ports in the chamber through which the anti-microbial fluid is suppliable to interior lumens of the article;

a tethered connection assembly for interconnection with the lumens of the article and the fluid ports, the tethered assembly including:

a first tube assembly having fittings at its ends, one fitting configured for interconnection with one of the fluid ports and the other fitting configured for interconnection with a lumen of the article, the tube assembly fittings configured for interconnection with the lumens and the plugs are configured to be sufficiently loose in structures that define ports to the lumens that a thin fluid passing gap is defined therebetween, at least one of (i) a second tube assembly with fittings and (ii) a plug configured for interconnection with a lumen of the article, and a tether which interconnects the tube assemblies and plugs.

11. The disinfection or sterilization system as set forth in claim 10 wherein the fluid chamber outlet are spray nozzles which are operated in at least two groups facilitating movement between the fittings and plugs and the structure defining the lumen ports.

12. The fluid disinfection or sterilization system as set forth in claim 10 wherein the fluid ports include a closure valve which has an open state and a leaky closed state that substantially but not completely closes the fluid outlet port when not interconnected with a fitting.

13. A tethered interconnection assembly for interconnecting lumens of endoscopes with anti-microbial fluid discharge ports of a fluid disinfection or sterilization system, the tethered connector assembly comprising:

a tether;

a first tube assembly connected with the tether including a tube, a fitting at one end configured for interconnection with a first anti-microbial fluid discharge port, and a fitting at another end configured for interconnection with surfaces surrounding a first lumen port on the endoscope;

a second tube assembly connected with the tether including a tube, a fitting at one end configured for interconnection with a second anti-microbial fluid discharge port, and a fitting at another end configured for interconnection with surfaces adjacent a second lumen port on the endoscope;

at least one plug connected with the tether and configured for interconnection with the surfaces surrounding a third endoscope lumen port; and an indicia associated with the tether for indicating at least one of a model of endoscope and family of endoscope models with which the tether assembly is to be used.

14. The tether assembly as set forth in claim 13 further including a plurality of tube assemblies and a plurality of plugs, each interconnected with the tether.

15. A tethered interconnection assembly for interconnecting lumens of endoscopes with anti-microbial fluid discharge ports of a fluid disinfection or sterilization system, the tethered interconnection assembly comprising:

a tether;

at least one tube assembly connected with the tether including a tube, a fitting at one end configured for interconnection with an anti-microbial fluid discharge port, and a fitting at another end configured for interconnection with surfaces surrounding a lumen port on the endoscope;

at least one plug connected with the tether and configured for interconnection with the surfaces surrounding one of the endoscope lumen ports, each of the tube assemblies and plugs including indicia of a prescribed interconnection order and being attached to the tether in accordance with the prescribed interconnection order; and an indicia associated with the tether for indicating at least one of a model of endoscope and family of endoscope models with which the tether assembly is to be used.

16. A tether assembly for interconnecting lumens of an endoscope with anti-microbial fluid discharge ports of a fluid disinfection or sterilization system, the tethered connector assembly comprising:

a tether;

a plurality of tube assemblies connected with the tether, each tube assembly including a tube, a fitting at one end configured for interconnection with an anti-microbial fluid discharge port, and a fitting at another end configured for interconnection with surfaces surrounding a lumen port on the endoscope;

the tube assemblies being interconnected with the tether in an appropriate order and spacing such that the tether allows each of the tubes to just reach a corresponding lumen port on the endoscope while not reaching sufficiently far for at least some of the tubes to reach non-corresponding lumen ports on the endoscope; and an indicia associated with the tether for indicating at least one of a model of endoscope and family of endoscope models with which the tether assembly is to be used.

17. A tether assembly for interconnecting lumens of an endoscope with anti-microbial fluid discharge ports of a fluid disinfection or sterilization system, the tethered connector assembly comprising:

a tether;

at least one tube assembly connected with the tether including a tube, a fitting at one end configured for interconnection with an anti-microbial fluid discharge port, and a fitting at another end configured for interconnection with surfaces surrounding a lumen port on the endoscope;

at least one of a plug and a further tube assembly connected with the tether and configured for interconnection with the surfaces surrounding one of the endoscope lumen ports; and a tag connected with the tether, an indicia recorded on the tag for indicating at least one of a model of endoscope and family of endoscope models with which the tether assembly is to be used and the tag further including a diagram illustrating proper interconnection of the tube assemblies and the plugs with the endoscope lumen ports.

18. A tether assembly for interconnecting lumens of endoscopes with anti-microbial fluid discharge ports of a fluid disinfection or sterilization system, the tethered connector assembly comprising:

a tether;

at least one tube assembly connected with the tether including a tube, a fitting at one end configured for interconnection with an anti-microbial fluid discharge port, and a fitting at another end configured for interconnection with surfaces surrounding a lumen port on the endoscope;

at least one of a plug and a further tube assembly connected with the tether and configured for interconnection with the surfaces surrounding at least one of the endoscope lumen ports, the fittings and the plugs being configured for interconnection with the surfaces surrounding endoscope lumen ports which interconnections are sufficiently loose that a thin gap is defined between (i) the fittings and the plugs and (ii) the surfaces surrounding the lumen ports; and an indicia associated with the tether for indicating at least one of a model of endoscope and family of endoscope models with which the tether assembly is to be used.

19. The tether assembly as set forth in claim 18 wherein at least one of the fittings and the plugs includes a conical tapered surface configured to be received partially in a lumen port of the endoscope and interconnection structure for holding the conical assembly partially received in the port and with a thin gap between the conical surface and the port.

20. The tether assembly as set forth in claim 18 wherein at least one of the fittings and the plugs includes a C-ring dimensioned to snap past an inward lip on a lumen port and be loosely received in the interior of the lumen.

21. The tether assembly as set forth in claim 18 wherein at least one of the plugs is configured to be received loosely within the surfaces surrounding the lumen port and further including a mounting assembly for loosely engaging structures on the endoscope to hold the plug within the port while permitting the plug to wobble.

22. The tether assembly as set forth in claim 18 wherein at least one of the fittings and plugs includes threads configured to loosely engage mating threads on an endoscope lumen port, the two sets of threads engaging sufficiently to hold the fitting or plug to the surfaces surrounding the port yet sufficiently loosely that a fluid flow path is defined therebetween.

23. A set of tether assemblies for connecting each of a plurality of lumened instruments with at least one of anti-microbial and cleaning fluid discharge ports of a reprocessor system, the assemblies including:
- a first tube assembly including a tube with a first fitting at one end configured for interconnection with a fluid discharge port and with a second fitting at another end configured for interconnection with surfaces surrounding a lumen port on the device; and,
- an indicia associated with the tube assembly for indicating at least one of a model and a family of models of devices with which the tube assembly is to be used;
- some of the tube assemblies further including:
  - a tether connected with the first tube assembly; and,
  - at least one of (i) a plug connected with the tether and configured for interconnection with surfaces surrounding another lumen port on the device and (ii) at least one additional tube assembly with another fitting for a connection with a processor port and with a further fitting configured for interconnection with surfaces surrounding a further lumen port on the device.

24. A fluid disinfection or sterilization system comprising:
- a chamber for receiving a lumened article to be microbially decontaminated;
- a plurality of first fluid outlets in the chamber for directing anti-microbial fluid over exterior surfaces of the article;
- at least one second fluid outlet for discharging anti-microbial fluid and configured for interconnection with a first fitting; and
- a tube assembly for interconnecting the second fluid outlet with surfaces adjacent a port to a lumen in the article, the tube assembly including:
  - a tube;
  - the first fitting connected to one end of the tube; and
  - a second fitting connected with the tube and configured for loose interconnection with the surfaces adjacent the lumen port in such a manner that (i) some of the anti-microbial fluid flows into the lumen and (ii) a remainder of the anti-microbial fluid flows between the fitting and the surfaces adjacent the lumen port, the interconnection being sufficiently loose that the fitting wobbles changing momentary points of contact with the surfaces adjacent the lumen port.

25. The system as set forth in claim 24 wherein the second fluid outlet has two states: an open state and a leaky closed state that permits a limited discharge of the anti-microbial fluid therethrough.

26. The system as set forth in claim 24 further including:
- a plug configured for loose interconnection with surfaces adjacent another lumen port in such a manner that a fraction of anti-microbial fluid flowing through the lumen flows between the plug and the surfaces adjacent the another lumen port.

27. A method of disinfection or sterilization of an article having interior lumens, the method comprising:
- identifying the article;
- selecting a tethered array of tubing assemblies which carry (1) an indicia corresponding to the identified article and (2) a diagram illustrating proper interconnection of the tethered array of tubing assemblies with the identified article and anti-microbial fluid outlets of a treatment chamber;
- placing the article in the chamber;
- interconnecting lumen ports of the article which provide access to its lumens with the anti-microbial fluid outlet with tubing assemblies in accordance with the diagram, including:
  - connecting a first fitting of a first tubing assembly of the tethered array with a first lumen port in accordance with the diagram, and
  - connecting a second fitting of the first tubing assembly with a first fluid outlet in accordance with the diagram,
  - connecting a first fitting of a second tubing assembly of the tethered array with a second lumen port in accordance with the diagram, and
  - connecting a second fitting of the second tubing assembly with a second fluid outlet in accordance with the diagram, the first and second tubing assemblies being tethered together;
- wetting an exterior of the article with an anti-microbial fluid and flowing the anti-microbial fluid through the tubing assembly and the lumen;
- disconnecting the first fittings of the tubing assemblies from the first and second lumen ports; and
- disconnecting the second fittings of the tubing assemblies from the first and second fluid outlets.

28. A method of disinfection or sterilization of an article having a plurality of interior lumens, the method comprising:
- providing a tethered assembly comprising tubing assemblies and at least one plug, the tubing assemblies and plugs being tethered together, the tethered assembly including an indicia indicating an order of interconnection of the tubing assemblies and plugs;
- connecting each tubing assembly of the tethered assembly of the tubing assemblies between one of the anti-microbial outlets and one of the lumen ports according to the interconnection order, including:
  - interconnecting a lumen port of the article which provides access to its lumen with an anti-microbial fluid outlet with a tubing assembly;
- connecting at least one plug with a lumen port;
- wetting an exterior of the article with an anti-microbial fluid; and
- flowing the anti-microbial fluid through the tubing assemblies and the lumens.

29. The method as set forth in claim 27 wherein the step of interconnecting the tubing assembly with the lumen port includes interconnecting the tubing assembly and the lumen port such that a first fraction of the fluid flows into the lumen and a second fraction of the fluid flows between the tube assembly and the lumen port.

30. A fluid disinfection or sterilization system comprising:
- a chamber for receiving a lumened article to be microbially decontaminated;
- at least one fluid outlet in the chamber for directing an anti-microbial fluid over exterior surfaces of the article;
- at least one fluid port in the chamber through which the anti-microbial fluid is suppliable to interior lumens of the article;
- a connection assembly for interconnection with the lumens of the article and the at least one fluid ports, the assembly including:
  - a first tube assembly having fittings at its ends, one fitting configured for interconnection with the at least one fluid port and the other fitting configured for interconnection with a lumen of the article, the fitting configured for interconnection with the lumen being configured to be sufficiently loosely connected with a structure defining a lumen port as to provide a thin gap therebetween such that a portion of the anti-microbial fluid flows between the fitting and the structure defining the lumen ports.

31. The fluid disinfection or sterilization system as set forth in claim 30, further including:

at least one of (i) a second tube assembly with fittings and (ii) a plug configured for interconnection with a second lumen of the article; and a tether which interconnects the tube assemblies and plugs.

32. The fluid disinfection or sterilization system as set forth in claim 31 wherein the article to be microbially decontaminated is an endoscope.

* * * * *

UNITED STATES PATENT AND TRADEMARK OFFICE
CERTIFICATE OF CORRECTION

PATENT NO. : 6,485,684 B1
DATED : November 26, 2002
INVENTOR(S) : Mapson et al.

It is certified that error appears in the above-identified patent and that said Letters Patent is hereby corrected as shown below:

The Title page showing an illustrative figure should be deleted and substituted for therefore the attatched Title page.

The Drawing sheets consisting of figures 1-11 should be deleted to be replaced with the Drawing sheets consisting of figures 1-11 as shown on the attached pages.

Signed and Sealed this

Twentieth Day of May, 2003

JAMES E. ROGAN
*Director of the United States Patent and Trademark Office*

(12) United States Patent
Mapson et al.

(10) Patent No.: US 6,485,684 B1
(45) Date of Patent: Nov. 26, 2002

(54) FLUID CONNECTION SYSTEM FOR ENDOSCOPE REPROCESSING WITH CONTROLLED LEAKAGE

(75) Inventors: Tara Denise Mapson, Cleveland; Yury Keselman, Beachwood; David Jesurun, South Euclid; Victor M. Selig, Euclid; Joseph Tvergyak, Chardon; Richard A. Schieman, Novelty; Bruce L. Vavra, Wickliffe, all of OH (US); Joseph T. Sestak, Erie, PA (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/499,134

(22) Filed: Feb. 7, 2000

(51) Int. Cl.$^7$ .................................................. A61L 2/00
(52) U.S. Cl. ...................... 422/28; 206/210; 206/370; 206/438; 422/292; 422/297; 422/300
(58) Field of Search ................... 422/300, 297, 422/292, 28; 206/210, 370, 438; 600/133

(56) References Cited

U.S. PATENT DOCUMENTS

| | | |
|---|---|---|
| 4,281,674 A | 8/1981 | Tanaka et al. |
| 4,299,244 A | 11/1981 | Hirai ........................... 134/102 |
| 4,552,728 A | 11/1985 | Taylor |
| 4,637,378 A | 1/1987 | Sasa .............................. 128/4 |
| 5,279,799 A | 1/1994 | Moser |
| 5,505,218 A | 4/1996 | Steinhauser et al. ....... 134/95.1 |
| 5,525,314 A * | 6/1996 | Hurson ......................... 422/300 |
| 5,552,115 A | 9/1996 | Malchesky ..................... 422/28 |
| 5,759,490 A | 6/1998 | Malchesky |
| 5,833,935 A | 11/1998 | Malchesky ................... 422/300 |
| 5,843,388 A * | 12/1998 | Arroyo ......................... 422/300 |
| 6,041,794 A | 3/2000 | Lin et al. .................... 134/22.11 |
| 6,068,815 A | 5/2000 | Oberleitner et al. |

FOREIGN PATENT DOCUMENTS

| | | |
|---|---|---|
| DE | 3416743 | 7/1985 |
| DE | 3538744 | 4/1986 |
| EP | 0 835 665 | 4/1998 |
| EP | 0 945 140 | 9/1999 |

* cited by examiner

*Primary Examiner*—Krisanne Thornton
(74) *Attorney, Agent, or Firm*—Fay, Sharpe, Fagan, Minnich & McKee, LLP (57) ABSTRACT

A fluid disinfection or sterilization system includes spray nozzles (26) for spraying an anti-microbial fluid on the exterior of an endoscope (14) supported in a microbial decontamination chamber (10a, 10b). The endoscope includes interior lumens which are microbially decontaminated by flowing anti-microbial fluid from outlets (28) through the lumens. A port (36) is connected with a leak detector. In order to ensure that the proper leak detector and anti-microbial fluid ports of the disinfection or sterilization system are interconnected with the proper lumen ports of the endoscope, a tethered connection assembly (50) is provided. The tethered interconnection assembly includes fittings (60, 62, 64) which are uniquely configured for interconnection with an appropriate one of a high pressure port, a low pressure port, and the leak detector port. Fittings at the other end of the tube assemblies (56) are configured for interconnection with appropriate corresponding ports of the endoscope. The tube assemblies (56) are interconnected by a tether (52) to which plurality of plugs (58) for plugging appropriate ports of the endoscope are also connected. A tag (54) identifies the model(s) of endoscope that the tethered connection assembly is to be used with and provides a diagram showing the proper interconnection pattern.

32 Claims, 4 Drawing Sheets